United States Patent [19]
Fuller et al.

[11] Patent Number: 6,063,600
[45] Date of Patent: *May 16, 2000

[54] DNA ENCODING CANINE INTERLEUKIN-1 RECEPTOR ANTAGONIST

[75] Inventors: Gerald Maxwell Fuller, Birmingham; Nelson Luis Fuentes, Bham, both of Ala.

[73] Assignee: UAB Research Foundation, Birmingham, Ala.

[ * ] Notice: This patent issued on a continued prosecution application filed under 37 CFR 1.53(d), and is subject to the twenty year patent term provisions of 35 U.S.C. 154(a)(2).

[21] Appl. No.: 08/862,730

[22] Filed: May 23, 1997

[51] Int. Cl.$^7$ .............................. C12N 15/24; C12N 15/00

[52] U.S. Cl. .................... 435/69.52; 435/69.1; 435/69.5; 435/252.3; 435/320.1; 536/23.5

[58] Field of Search .......................... 536/23.5; 435/69.5, 435/69.52, 252.3, 320.1

[56] References Cited

U.S. PATENT DOCUMENTS

| | | |
|---|---|---|
| Re. 35,450 | 2/1997 | Dower et al. . |
| 4,894,333 | 1/1990 | Cerretti et al. . |
| 4,902,708 | 2/1990 | Kim . |
| 4,968,607 | 11/1990 | Dower et al. . |
| 4,975,464 | 12/1990 | Imaki et al. . |
| 5,075,222 | 12/1991 | Hannum et al. ...................... 435/619.1 |
| 5,081,228 | 1/1992 | Dower et al. . |
| 5,180,812 | 1/1993 | Dower et al. . |
| 5,196,402 | 3/1993 | Braganza et al. . |
| 5,220,018 | 6/1993 | Bock et al. . |
| 5,286,739 | 2/1994 | Kilbourn et al. . |
| 5,286,847 | 2/1994 | Gehrke et al. ........................... 530/357 |
| 5,296,592 | 3/1994 | Dower et al. . |
| 5,319,071 | 6/1994 | Dower et al. . |
| 5,334,380 | 8/1994 | Kilbourn et al. . |
| 5,350,683 | 9/1994 | Sims et al. . |
| 5,455,330 | 10/1995 | Haskill et al. ........................... 530/351 |
| 5,464,937 | 11/1995 | Sims et al. . |
| 5,488,032 | 1/1996 | Dower et al. . |
| 5,492,888 | 2/1996 | Dower et al. . |
| 5,508,262 | 4/1996 | Norman . |
| 5,552,536 | 9/1996 | Nicholson et al. . |
| 5,563,046 | 10/1996 | Mascarenhas et al. . |

OTHER PUBLICATIONS

Lebedenko et al, *Bioorg. Khim* 1993, 19(8) 586–88.
Haskill et al, *PNAS* 1991, 88(a), 368–85.
Caron et al., "Chondroprotective effect of intraarticular injections of interleukin–1 receptor antagonist in experimental osteoarthritis. Suppression of collagenase–1 expression," *Arthritis and Rheumatism*, 1996; 39:1535–1544.
Femandes, et al., "Effects of tenidap on the progression of osteoarthritic lesions in a canine experimental model. Suppression of metalloprotease and interleukin–1 activity," *Arthritis and Rheumatism*, 1997; 40:284–294.
Fischer, et al.,"'Comparison between effects of interleukin–1 administration and sublethal endotoxemia in primates, *the American Physiological Society*, 1991:R442–R452.
Granowitz, et al., "Pharmacokinetics, Safety and Immunomodulatory Effects of Human Recombinant Interleukin–1 Receptor Antagonist in Healthy Humans," *Cytokine*, 1992 4(5):353–360.
Houssiau, "Cytokines in rheumatoid arthritis," *Clinical Rheumatology*, 1995 14 Suppl. 2:10–3.
Pickvance, et al., "Immunolocalization of selected cytokines and protease in canine articular cartilage after transarticular loading," *J. of Ortho. Res.*, 1993; 11(3):313–323.
Shuster, et al., "Administration of recombinant human interleukin 1 receptor antagonist during endotoxin–induced mastitis in cows," *American Journal of Veterinary Research*, 1995; 56:313–320.
Charles A. Dinarello, M.D., Supplement to Nutrition, 1995, vol. 11, No. 5: 492–497.
C. H. Evans and P. D. Robbins, Annals of Medicine, 1995, 27:543–546.
J. Lewthwait, Journal of Rheumatology, Mar, 21(3):467–72.
Fabio Cominelli, The Journal of Biological Chemistry, Mar. 4, 1994, vol. 269, pp. 6962–6971.
GL Hung, Gene Thereapy, Jan. 1994, 1(1):64–9.
Kamyar A. Zahedi, Cytokine, Jan. 1994, vol. 6, No. 1, pp. 1–9.
Koichhi Aiura, Infection and Immunity, Aug. 1993, vol. 61, No. 8, pp. 3342–3350.
J. Martel–Pelletier, Biochimica et Biophsica Acta., Feb. 17, 1993, 1175(3):302–305.
James A. Lederer, Journal of Leukocyte Biology, Jun., 1992, vol. 51, pp. 586–590.
Eva Fischer, Journal of Clinical Investigation, May, 1992, vol. 89, pp. 1551–1557.
F. Goto, Immunology, 1992, vol. 77, pp. 235–244.
Andrew Lennard, Cytokine, Mar., 1992, vol. 4, No. 2, pp. 83–89.
Hitoshi Matsuchime, Blood, Aug. 1, 1991, vol. 78, No. 3, pp. 616–623.
Charles A. Dinarello, Blood, Apr. 15, 1991, vol. 77, No. 8, pp. 1627–1652.
Go Wakabayashi, The FASEB Journal, Mar., 1991, vol. 5, pp. 338–343.
S.P. Eisenberg, Proc. Natl. Acad. Sci. USA, Jun. 1991, Immunology, vol. 88, pp. 5232–5236.
Kjell Ohlsson, Nature, Dec. 6, 1990, vol. 348, pp. 550–552.
D. B. Carter, Nature, Apr. 12, 1990, vol. 344, pp. 633–638.
Stephen B. Eisenberg, Nature, Jan. 25, 1990, vol. 343, pp. 341–346.
E. J. Sillenaar Bilgen, Transplantation Proceedings, Feb., 1989, vol. 21, No. 1, pp. 2829–2830.
C. Natanson, Journal of clinical Investigation, Jan., 1989, 83(1):243–251.
Seijiro Okusawa, Journal of Clinical Investigation, Apr., 1988, vol. 81, pp. 1162–1172.
Anders Waage, Journal of Experimental Medicine, Jun., 1988, vol. 167, pp. 1987–1992.
H. Okayama, Molecular & Cellular Biology, Feb., 1983, 3(2):280–289.
W. David Benton, Science, vol. 196, Apr. 8, 1977, pp. 180–182.

*Primary Examiner*—Garnette D. Draper
*Attorney, Agent, or Firm*—Alana Kriegsman; Bruce D. Gray; Kilpatrick Stockton, LLP

[57] ABSTRACT

Canine IL-1 receptor antagonist protein, DNAs, and expression vectors carrying DNA sequence encoding canine IL-1 receptor antagonist are disclosed.

30 Claims, 5 Drawing Sheets

Fig 1.

```
ACGGCTGCGA GAAGACGACA GAAGGGGGCA GTGTCCCGTT GCCTCGCTGT GGCCACCGAA    60
TGGAAACCTG CAGGTGTCCT CTCAGCTACC TAATCTCTTT CCTCCTTTTC CTGCCCCATT   120
                         Seq 18
CAGAGACAGC CTGCCGTCCC TTGGGGAAGA GACCTTGCAG GATGCAAGCC TTCAGAATCT   180
     Seq 12
GGGATGTTAA CCAGAAGACC TTCTACCTGA GGAATAACCA ACTAGTCGCT GGATACTTGC   240
AAGGATCAAA TACTAAATTA GAAGAGAAGT TAGATGTGGT GCCCGTCGAG CCTCATGCCG   300
TGTTCTTGGG GATCCATGGG GGGAAGCTGT GCCTGGCCTG TGTCAAGTCT GGAGATGAGA   360
      Seq 16
CCAGGCTCCA GCTGGAGGCC GTTAACATCA CTGACCTGAG TAAGAACAAG GATCAAGACA   420
                              Seq 14
AGCGCTTTAC CTTCATCCTC TCAGACAGTG GCCCCACCAC CAGCTTTGAG TCTGCTGCCT   480
                                              Seq 17
GCCCTGGCTG GTTCCTCTGC ACAGCACTGG AGGCCGACCG GCCTGTCAGC CTCACCAACA   540
                                                     Seq 19
GACCAGAAGA GGCCATGATG GTCACTAAGT TCTACTTCCA GAAGGAATAA TAGTGTGTCC   600
    GAA
ATTCCGTGCT TCCCCCCCAC TCCCAACACA TCAATGACTC CAGAGATGCC TCTCCATTCT   660
                                                      Seq 10
GCCTGGGGTC TCCTGGCTGT GGTGGAGGCT CTGAGGAGCA GCCTCGGTGG GGTGGACCCT   720
CAGAAGGATG TATGAGAGCC CTGGTAACGG GACCCTGCCT CCAGCCTCCT CAGCTAGCCA   780
ACCTCAATGC TGCCACCACA GTGGTCTTTC TAAAGTGCAC CTCTAGCTGC AGCACTGCTC   840
CAGGCCTTTC AGGGCTGCCT CTGCCTTCTG GATTAAAGCC AGGCTGCTTG GCCAGCCTGG   900
CCCCCTGCTC TCCTCTCCGT AACTCCTTGC TCTCCTCCCT TGCCCCATGT CCATGTCCTG   960
GATCCCTCCT GCCCCTTTGC TGGCCTCCCA AACCTTGTGT TTTGCAAACC GATGCTGTTC  1020
TGTGGGGAAA CCTTAGAGTC TGTGCCAAGA TGGCCGCTAA GGATTTCAAC TTGGCTTTCC  1080
TTTGAAGCCA ATTTCATCCA GTTTCAAGGG AGAGTCCTTT ATTTAGACAC TATGTCCATT  1140
CTGGAAANGT GTGGGCAAGG ATGAAAAGTA GCTCTCCCTT TTGATTTCTC TTATTTTTGA  1200
ACGTCCTGAC CTGCAAAAAT GACAAGTTAG TGTGTTATGT TGGTCTCTAC TTTTTTTCTT  1260
TCTGTGATGT TCCTAAAGCC TGGCCCCACT GCTCCAGCGA GGTACCATTT CCACTCCAGG  1320
                                   Seq 11
CCTTTGACAG CCACCTGCAG TGCTTGTCCT CCCCATCTCT CCCATCAAAA CTCCCAGCTG  1380
CAGGCCAGGG CATCAATGTG GCTCCACTGT TCCTGGGAGG GAGGAATTAC TCTCGGACCA  1440
TTTTACACTT CTGACACTCT GAGACTTGTT TGAAAGGTTG TGTCTCTGTC TGTCTCCCAC  1500
ACCAGACTGT GAGTTCCCAA GAGAAGGGAG CATGACCTCT GTGTTTTGGG GCTCCCGCAG  1560
                                                  Seq 13
GGCTGAGCAC ACAGCTCCGG CCCTTAGCAC GTGCTCACTG AATGTGTGTT GTATGTGTTG  1620
AGTAGAAAGG TTTTTACTTT TTGTGAATTA AGGTTTGTTT TACAATAAAA TTTTAAAAAT  1680
TCAAAAAAAA AAAAAAAAAA AAAAAAAAA                                   1710
```

Fig 3

```
                                                                                                         MATURE N-TERMINUS
MOUSE   1  ATGGAAATCTGCTGGGGACCCTACAGTCACCTAATCTCTCCTTCTCTGTTTCATTCAGAGGCAGCCTGC  CGCCCTTCTGGGAAAAGACCCT
RAT        ATGGAAATCTGCAGGGGACCTTACAGTCACCTAATCTCTCCTTCTCTGTTCTGTTCAGAGTCAGCAGCTGGC  CACCCTGCTGGGAAAAGACCCT
HUMAN      ATGGAAATCTGCAGAGGCCTCCGCAGTCAGTCAATCACTCTCCTCCTCCTG    TTCCATTCAGAGACGATCGC  CGACCCTCTGGGAGAAAATCCA
CANINE     ATGGAAACCTGCAGTGTCCTCTCAGCTACCTAGTCTCTTTCCTCCTTTCCTG     CCCCATTCAGAGACAGCCTGC  CGTCCCTTGGGGAAGAGACCTT
RABBIT     ATGAGACCCCCAGGAGACCACCGCAGGCACCTAATCTCCTCCTCCTCCTG      TTCCATTCAGAGACAGCCTGC  CGCCCTTCTGGGAAAAGACCTT

101        GCAAGATGCAAGCCTTCAG AATCTGGGATACTAACCAGAAGACCTTTACCTGAGAAACAACCAGTCATTGCTGGGTACTTACAAGGACCAAATATCAA
           GCAAGATGCAAGCCTTCAG AATCTGGGATACTAACCAGAAGACCTTTACCTGAGAAACAACCAGTCATTGCTGGGTACTTACAAGGACCAAATATCAA
           GCAAGATGCAAGCCTTCAG AATCTGGGATGTTAACCAGAAGACCTTCTACCTGAGGAACAACCAGTCATTGCTGGGTACTTACAAGGACCAAATACCAA
           GCAGGATGCAAGCCTTCAG AATCTGGGATGTTAACCAGAAGACCTTTAACCTGAGGAACAACCAGTCATTGCTGGGATACTGCAAGGACCAAATGTCAA
           GCAGGATGCAGGCCTTCAG AATCTGGGATGTTAACCAGAAGACCTTCTACCTGAGGAATAACCAACTAGTGCTGCTGGATACTGCAAGGATCAAATACTAA
                         I 1                                  GCAGGATGCAGGCCTTCAG AATCTGGGATGTTAACCAGAAGACCTTCTACCTGAGGAAGACCAACTAGTCGTCGTCGGTTACTTGCAAGGCCCAAATGCCAA

201        ACTAGAAG AAAAGATAGACATGGTAG GAAGTTAACATCACTGATCTGAGCAAGAACAAAGAAGAAGAACAAGCGCTTTACTTCATCCGCTCCTGAGAAAGGCCCCA
           ACTAGAAG AAAAGATAGACATGGTGGTGCCTATTGACTTTCAGCCTCATGCTCGTGTTCTGGGAATGCTCTGTTCTGTTGTCCTGTGTCAAGTCTGGTGAT
           TTTAGAAG AAAAGATAGATGTGGTAG TACCCATTGACTTTGAGCCTCATGCTCTGTTCTGGGAATGCTCTGTCCTGTCCTGGCCTGTCTGTCAAGTCTGTGAT
           ATTAGAAG AGAAGTTAGATGTGGTGCC GCCGTTAACATCACTGACCTGACCTGAGTAAGAACAAGAGGATCAAGACAAGACAAGAACAAGAAGAAGAAGAAGAAGCCTAA
           ATTAGAAG AAAGGATAGATGTGGTGCC GCCGTTAACATCACTGACCTGGGCAAGAACCTGGGCAAGAACTGGGCAAGAGAGAACAAGAAGAAGAACAAGAAGCCTAA
                         I 2                   I 3

301        GATATCAAGCTCCAGCTGGAG GAAGTTAACATCACTGATCTGAGCAAGAACAAAGAAGAAGAACAAGCGCTTTACTTCATCCGCTCCTGAGAAAGGCCCCA
           GACACCAAGCTCCAGCTGGAG GAGGTTAACATCACTGATCTGAACAAGAACAAGAACAAGAACAAGCTTGCTTACTTCATCCGCTCCTGAGAAAGGCCCCA
           GAGACCAGCTCCAGCTGGAG GCAGTTAACATCACTGACCTGAGCGAGCAAGCTGAACAAGCGATGAAGCTGACCAGCCGTCGCCTTCGCCTTCACCTTCATCCTCCTTCAGACACGTGCCCCA
           GAGACCAGCTCCAGCTGGAG GCCGTTAACATCACTGACCTGACCTGAGTAAGAACAAGAGGATCAAGACAAGACAAGAACAAGAAGAAGAAGAAGAAGCCTAA
           AAGATGAAGCTCCATTGGAG GCCGTTAACATCACTGACCTGGGCAAGAACCTGGGCAAGAACTGGGCAAGAGAGAACAAGAAGAAGAACAAGAAGCCTAA

401        CCACCAGCTTTGAGTCAGCTCAGCTGCCTGTCCTGTCCAGGATGGTTCCTCTGCACAACACCGGAAGAGCCCCT
           CCACCAGCTTCGAATCACTTGCCTGCCTGTCCTGTCCAGGATGCTGTTCCTCTGCACAACACCGGAAAAGAGCCCTG
           CCACCAGTTTGAGTCTGCCGCCTGCCTGCCCGGTTGGTTCCTCTGCACAGCGATGGAAGCTGACGAGCTGACAGAGGCGT
           CCACCAGCTTGAGTCTGCTGCCTGCCTCCTGCCCGGCTGCGCCGCCTGGTTCCTGTCCTGCACAGCAGCCGGCCTGCAGCCCAGCAAGAGAGGCAT
           CCACCACCTTCGAGTCTGCTGCCTGCCTCCTGCCGGGCTGTTCTCGCACAGCCCTGACGGCCTGGAGGCTGACCAGCCGTTGACCAGCCAGTAG

501        TATAGTCACGAAGTTCTACTTCCAGGAAGACCAATAG                    537
           TACAGTCACAAAGTTCTACTTCCAGGAAGACCAATAG                    537
           CATGGTCACCAAATTCTACTTCCAGGAGGACGAGTAG                    534
           GATGGTCACTAAGTTCTACTTCCAGAAGGAATAATAG                    534
           CGTGGTCACCAAGTTCTACTTCCAGGAGGAGACCAGTAG                  534
```

Fig 4

```
RAT     MEICRGPYSHLISLLLILLFRSESAGHPAGKRPCKMQAFRIWDTNQKTFYLRNNQLIA
MOUSE   MEICWGPYSHLISLLLILLFHSEAACRPSGKRPCKMQAFRIWDTNQKTFYLRNNQLIA
HUMAN   MEICRGLRSHLITLLLF   LFHSETICRPSGRKSSKMQAFRIWDVNQKTFYLRNNQLVA
RABBIT  MRPSRSTRRHLISLLLF   LFHSETACRPSGKRPCRMQAFRIWDVNQKTFYLRNNQLVA
CANINE  METCRCPLSYLISFLLF   LPHSETACRPLGKRPCRMQAFRIWDVNQKTFYLRNNQLVA

GYLQGPNTKLEEKIDMVPIDFRNVFLGIHGGKLCLSCVKSGDDTKLQLEEVNITDLNK
        GYLQGPNIKLEEKIDMVPIDLHSVFLGIHGGKLCLSCAKSGDDIKLQLEEVNITDLSK
        GYLQGPNVNLEEKIDVVPIEPHALFLGIHGGKMCLSCVKSGDETRLQLEAVNITDLSE
        GYLQGPNAKLEERIDVVPLEPQLLFLGIQRGKLCLSCVKSGDKMKLHLEAVNITDLGK
        GYLQGSNTKLEEKLDVVPVEPHAVFLGIHGGKLCLACVKSGDETRLQLEAVNITDLSK

NKEEDKRFTFIRSETGPTTSFESLACPGWFLCTTLEADHPVSLTNTPKEPCTVTKFYFQEDQ
        NKEEDKRFTFIRSEKGPTTSFESAACPGWFLCTTLEADRPVSLTNTPEEPLIVTKFYFQEDQ
        NRKQDKRFAFIRSDSGPTTSFESAACPGWFLCTAMEADQPVSLTNMPDEGVMTKFYFQEDE
        NKEQDKRFTFIRSNSGPTTFESASCPGWFLCTALEADQPVSLTNTPDDSIVVTKFYFQEDQ
        NKDQDKRFTFILSDSGPTTSFESAACPGWFLCTALEADRPVSLTNRPEEAMMVTKFYFQKE
```

DNA ENCODING CANINE INTERLEUKIN-1 RECEPTOR ANTAGONIST

FIELD OF THE INVENTION

The present invention relates generally to cytokine receptor antagonists, and specifically, to cDNA encoding the Interleukin-1 receptor antagonist (IL-1ra) for canine species.

BACKGROUND OF THE INVENTION

Interleukin-1 ( IL-1) type cytokines and their respective receptors have been studied with much interest over the past ten years. Additionally, other molecular entities which have effect on or in association with the IL-1 cytokines and receptors have also drawn much interest. One such molecule has been a protein receptor antagonist now termed Interleukin -1 receptor antagonist (IL-1ra).

IL-1B is known to be a cytokine that triggers inflammatory processes (Dinarello C A, Interleukin-1 and Interleukin-1 Antagonism. *Blood* 1991; 77:1627–1652) The action of the receptor antagonist, IL-1ra, presently appears to generate its effect by competitively blocking the ligand (IL-1) for the receptor (Dinarello C A, Interleukin-1 and Interleukin-1 Receptor Antagonist. *Nutrition* 1995; 11: 492–494). Studies have indicated that IL-1ra may have important implications for use as a therapeutic agent in the treatment against inflammatory diseases including endotoxin-induced shock, pancreatitis, mastitis, and rheumatoid arthritis (Ohlsson K, Bjork P, Bergenfeldt M, Hageman R, and Thompson R, Interleukin-1 receptor antagonist reduces mortality from endotoxin shock. *Nature* 1990; 348: 550–552; U.S. Pat. No. 5,508,262 by Norman J G, Interleukin-1 receptor antagonist decreases severity of acute pancreatitis, 1996, University of South Florida, Tampa, Fla.: USA; Shuster D and Kehrli M, Administration of recombinant human interleukin 1 receptor antagonist during endotoxin-induced mastitis in cows. *American Journal of Veterinary Research* 1995; 56: 313–320; Evans C H and Robbins P D, Progress toward the Treatment of Arthritis by Gene Therapy. *Annals of Medicine* 1995; 27: 543–546). Such therapeutic administration has been contemplated using the protein or its antibody via several regimens including oral, intravenous, intraperitoneal, intranasal, and subcutaneous administration. Where arthritic conditions are contemplated, direct injection into the joints is contemplated to directly administer the protein to the disease site where the ligand appears to migrate and induce the inflammatory response of the arthritic condition. Intra-synovial expression of human IL-1ra in rabbits is protective against injection of human IL-1, however, use of human IL-1ra does not protect against rabbit IL-1 induced arthritis in rabbits (Hung G, Galea-Lauri J, Mueller G, Georgescu H, Larkin L, Suchanek M, Tindal M, Robbins P, and Evans C, Suppression of intra-articular responses to interleukin-1 by transfer of the interleukin-1 receptor antagonist gene to synovium. *Gene Therapy* 1994; 1: 64–69; Lewthwaite J, Blake S, Hardingham T, Warden P, and Henderson B, The effect of recombinant human interleukin 1 receptor antagonist on the induction phase of antigen induced arthritis in the rabbit. *Journal of Rheumatology* 1994; 21: 467–472). Human IL-1ra has been tried in bovine to reduce the inflammation of mammary gland (Shuster D and Kehrli M, Administration of recombinant human interleukin 1 receptor antagonist during endotoxin-induced mastitis in cows. *American Journal of Veterinary Research* 1995; 56: 313–320). However, although IL-1 bioactivity in milk was prevented, no effect of using human IL-1ra was shown in the bovine model. Moreover, human IL-1ra does not bind to bovine neutrophil IL-1 receptor (Lederer J and Czuprynski C, Characterization and identification of interleukin 1 receptors on bovine neutrophils. *Journal of Leukocyte Biology* 1992; 51: 586–590). Therefore, there is a direct indication in the art for a need to obtain species specific receptor antagonists for use against various disease states in which use of receptor antagonist is indicated to be useful in treatment of such disease states.

The IL-1ra gene sequence has been identified in several species. Protein and/or DNA sequence has been disclosed for, human, mouse, rabbit, and rat (Eisenberg SP, Evans R, Arend W, Verderber E, Brewer M, Hannum C, and Thompson R C, Primary structure and functional expression from complementary DNA of a human interleukin-1 receptor antagonist. *Nature* 1990; 343: 341–346; Carter D B, Deibel M R, Dunn C J, Tomich C-S, Laborde A L, Slightom J L, Berger A E, Bienkowski M J, Sun F F, McEwan R N, Harris K W, Yem A W, Waszak G A, Chosay J G, Sieu L C, Hardee M M, Zurcher-Neely H A, Reardon I M, Heinrikson R, Truesdell S, Shelly J, Eessalu T, Taylor B, and Tracey D, Purification, cloning, expression and biological characterization of an interleukin-1 receptor antagonist. *Nature* 1990; 344: 633–638; Lennard A, Gorman P, Carrier M, Griffiths S, Scotney H, Sheer D, and Solari R, Cloning and Chromosome Mapping of the Human Interleukin-1 Receptor Antagonist Gene. *Cytokine* 1992; 4 83–89; Matsushime H, Roussel M, Kouji M, Hishinuma A, and Sherr C, Cloning and Expression of Murine Interleukin-1 Receptor Antagonist in Macrophages Stimulated by Colony-Stimulating Factor 1. *Blood* 1991; 78: 616–623; Zahedi K, Uhlar C, Rits M, Prada A, and Whitehead A, The mouse interleukin 1 receptor antagonist protein: Gene structure and regulation in vitro. *Cytokine* 1994; 6: 1–9; Goto F, Goto K, Miyata T, Ohkawara S, Takao T, Furukawa S, Maeda T, Iwanaga S, Shimonishi Y, and Yoshinaga M, Interleukin-1 receptor antagonist in inflammatory exudate cells of rabbits. Production, purification and determination of primary structure. *Immunology* 1992; 77: 235–244; Cominelli F, Bortolami M, Pizarro T, Monsacchi L, Ferretti M, Brewer M, Eisenberg S; and Ng R, Rabbit Interleukin-1 Receptor Antagonist. *J. of Biol. Chem.* 1994; 269: 6962–6971). The protein sequences of the known species are very similar as noted in FIG. 4. As shown the Table I, the highest percent homology is between rat and mouse at 90% and the lowest homology is between human and rat at 75%. In the table, D=dog, H=human, M=mouse, RB=rabbit, and R=rat.

TABLE I

|    | R   | M   | H   | D   | RB  |
|----|-----|-----|-----|-----|-----|
| R  | 100 |     |     |     |     |
| M  | 90  | 100 |     |     |     |
| H  | 75  | 77  | 100 |     |     |
| D  | 74  | 74  | 80  | 100 |     |
| RB | 78  | 79  | 78  | 76  | 100 |

Thus, as indicated from the homologies, it is likely that species specific binding may be necessary for the canine IL-1ra protein to interact with its respective receptor molecule(s) to provide effective treatment for such clinical indications as IL-1 associated arthritis. As is typically the case concerning ligand, receptor, and a receptor antagonist binding, the variation in amino acid sequence is very important to the specific binding characteristics. Moreover, in a long-term treatment, small differences between the same protein in different species may give rise to an immune response. One objective of the current invention is to alleviate the likelihood of an immune response by obtaining canine IL-1ra to be used specifically in dog species.

In studying the effect of IL-1ra in treatment of various disease states, including arthritic conditions, canine species have been recognized as an appropriate animal model (Caron J F, Fernandes J C, Martel-Pelletier J, Tardif G, Mineau F, Geng C, Pelletier J P, Chondroprotective effect of intraarticular injections of interleukin-1 receptor antagonist in experimental osteoarthritis. Supression of collagenase-1 expression. *Arthritis and Rheumatism* 1996; 39: 1535–1544; Picvance E O, Oegema T R, Thompson R C, Immunolocalization of selected cytokines and proteases in canine articular cartilage after transarticular loading. *Journal of Orthopaedic Research* 1993; 11: 313–323; Fernandes J C, Caron J P, Martel-Pelletier J, Jonanovic D, Mineau F, Tardif G, Otterness I G, Pelletier J P, Effects of tenidap on the progression of osteoarthritic lesions in a canine experimental model. Suppresion of metalloprotease and interleukin-1 activity, *Arthritis and Rheumatism* 1997; 40: 284–294). Moreover, many breeds of dog are susceptible to arthritic disease and can benefit directly from advances in the art to treat canine arthritic conditions. The current invention advances such art through obtaining canine IL-1ra DNA sequence from which the protein may be produced for use in treatment of canine diseases including arthritis.

SUMMARY OF THE INVENTION

The present invention provides isolated natural gene sequence encoding canine IL-1ra. The invention also provides isolated canine IL-1ra protein. A further embodiment of the present invention provides for DNA sequences encoding IL-1ra, in particular, canine IL-1ra selected from the group consisting of (a) a cDNA clone having a nucleotide sequence encoding an amino acid sequence of amino acids −25 through 151 of SEQ ID NO.:4; (b) a DNA capable of hybridization to a clone of (a) under moderately stringent conditions and which encodes a biologically active canine IL-1ra molecule; and (c) a DNA having a sequence which is degenerate as a result of the genetic code to a DNA as defined in (a) or (b) above and which encodes biologically active canine IL-1ra molecules.

Another preferred embodiment of the invention contemplates recombinant expression vectors having the DNA sequences described above as well as the IL-1ra proteins encoded therein and expressed by the expression vectors and the processes of producing said proteins from said vectors. Yet another embodiment of the invention contemplates the purification of said proteins.

Still other objects of the invention include treating dogs susceptible to arthritic conditions by administration of an effective amount of the canine IL-1ra protein or the DNA by gene therapy.

BRIEF DESCRIPTION OF THE DRAWINGS

FIG. 1 is a single stranded nucleotide sequence depicting the cDNA retrieved from reverse transcription of canine mRNA encoding IL-1ra. The figure also depicts the locations of primers and direction of sequencing used to obtain the DNA sequence as well as to clone the cDNA into an expression vector. The sequence depicted is the same as SEQ ID NO 1.

FIG. 3 is a comparison of the DNA sequence of canine IL-1ra with that of the rat, mouse, rabbit, and human. The sequences are depicted beginning at the 5' initiation codon ATG and terminating with the nonsense codon at the 3' end. Notations I1, I2, and I3 depict locations of introns in species in which the genomic DNA sequence has been obtained. The figure further notes the location of the primers used for creating a PCR generated human sequence probe for obtaining the canine cDNA. DNA sequences for rat, mouse, rabbit and human are listed in sequence listing SEQ ID NOs 24 to 27.

FIG. 4 is a comparison of the full length canine IL-1ra peptide sequence with that of human, mouse, rabbit, and rat. The figure is presented in one letter amino acid code for necessity of clarity. A=Ala, N=Asn, D=Asp, R=Arg, C=Cys, Q=Gln, E=Glu, G=Gly, H=His, I=Ile, L=Leu, K=Lys, M=Met, F=Phe, P=Pro, S=Ser, T=Thr, W=Trp, Y=Tyr, V=Val. The sequences are listed in SEQ ID NOs 20 to 23.

DETAILED DESCRIPTION OF THE INVENTION

Figure 2:
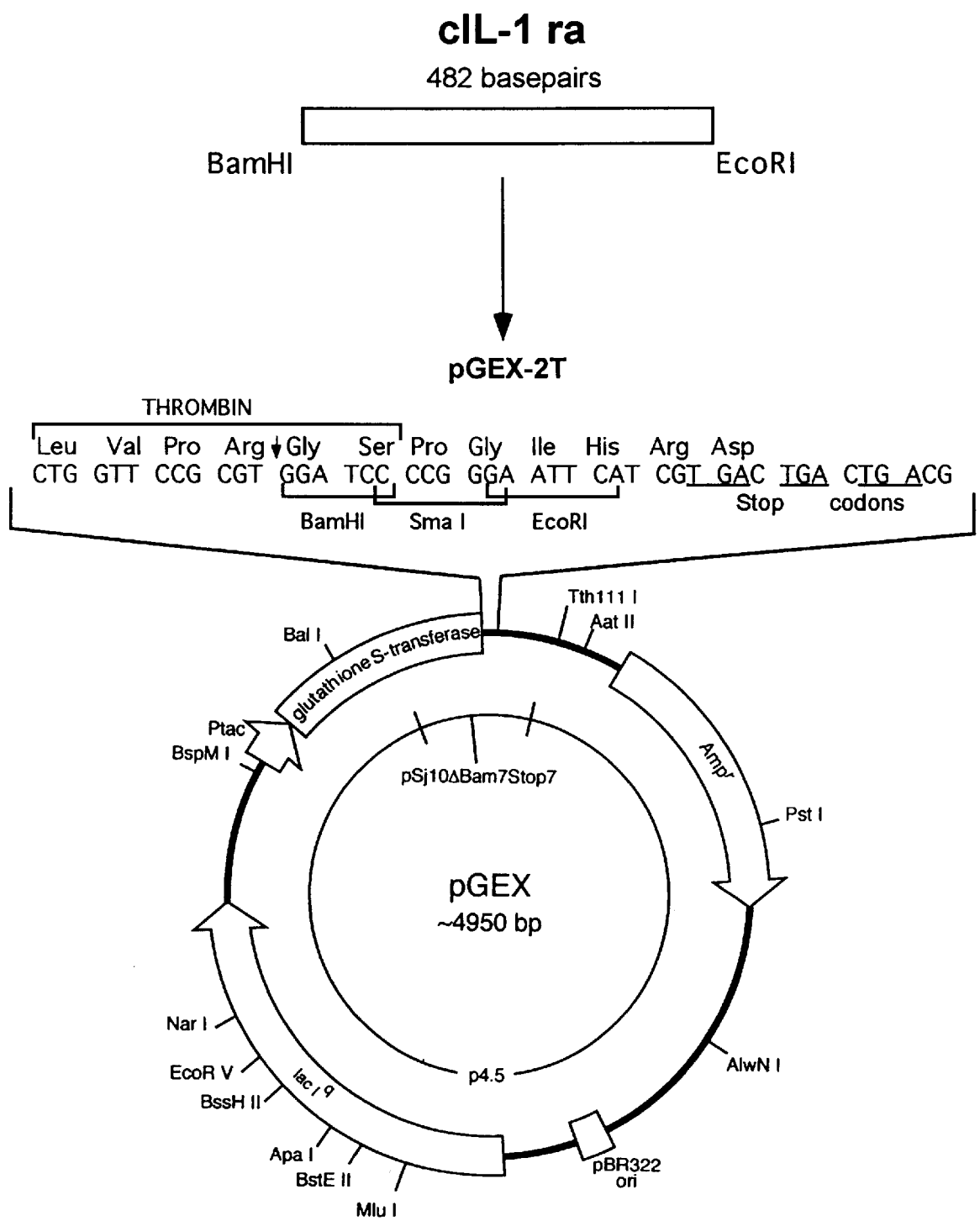
FIG. 2 represents a schematic diagram of the glutathione-S-transferase (GST) fusion protein expression construct plasmid pGEX-2T. The cDNA is inserted into the plasmid via the BamHI restriction site at the 5' and an EcoRI restriction site at the 3'.

Isolation and Identification of cDNA Sequence of canine IL-1ra General Cloning Techniques:

The materials and methods used to establish a cDNA library containing the cDNA sequence that encodes full length canine IL-1ra are well known in the recombinant DNA art. However, a general description of the materials and methods used in the current invention is presented for clarity.

Preferred embodiment for a canine cDNA library and screening thereof

White blood cells were isolated from fresh dog blood by layering whole blood on an isotonic solution of Accudenz (Accurate Chemical N.Y.) 60% in HBSS buffer. The white blood cells obtained after centrifugation were plated and incubated in RPMI media 10% FBS. After 2 hours incubation at 37° C., the media was gently aspirated. Fresh media was added and the remaining adherent macrophages were incubated overnight at 37° C., 5% $CO_2$.

Following overnight incubation, the cells were stimulated with LPS(20 ug/ml) in fresh media for 6 hours. RNA was extracted and purified utilizing standard guanidine thiocyanate/oligo (dT) priming protocol as described (Okayama H, Berg P, A cDNA cloning vector that permits expression of cDNA inserts in mammalian cells. *Molecular and Cellular Biology* 1983; 3: 280–289). An aliquot of the isolated oligo (dT) RNA was electrophoresed to examine the quality of the RNA. After determining the quality and quantity of the RNA, 20 ug was used to construct a cDNA library.

The cDNA library cloning materials utilized that of Clontech, (Palo Alto, Calif.) to construct an oligo(dT) primed lambda gt11 library. The cDNA was blunt end ligated to adaptors which contained Eco RI restriction sites. The cDNA was then ligated to the lambda gt11 using Eco R1 restriction site through the adaptor. The library was screened according to standard techniques such as that described (Sambrook J F, Frisch E F, Maniatis T, *Molecular cloning,*

*a Laboratory Manual.* Cold Spring Harbor Laboratory Press. Cold Spring Harbor. 1989) using as a hybridization probe human IL-1ra DNA sequence amplified by RT-PCR. The primer sequences used for creating the human probe are designated in the sequence listing by SEQ ID NO. 6 and SEQ ID NO 7. These sequences conform to the human IL-1ra beginning from the mature protein codon for the 5' probe of SEQ ID NO 6 and beginning from the termination codon at the 5' end of SEQ ID NO 7.

The largest clone (designated c IL-1ra) as determined by agarose gel was 1.7 kb. This clone was subcloned into M13 mp18 vector via the Eco R1 restriction site and DNA sequence analysis was carried out using the Perkin-Elmer Applied Biosystem 377 Sequencer. Oligonucleotides used as sequencing primers and described in SEQ ID Nos. 8 to 17 were synthesized by Integrated DNA Technologies (Coralville, Iowa). Sequence data were analyzed using the University of Wisconsin Genetic Computer Group Program on a VAX DCL computer.

Analysis of the cDNA IL-1ra Clones

The cDNA obtained for full length canine IL-1ra contains 1710 nucleotides and one open reading frame with 528 nucleotides. The polyadenylation signal is 1071 bases 3' to the stop codon and 13 base upstream of the poly (A) tail. The open reading frame (ORF) is preceded by 59 nucleotides of untranslated region (UTR) and is followed by a 3' UTR of 1092 nucleotides excluding the poly(A)tail.

The intron organization is believed to be similar to those found in human, mouse, rat and rabbit IL-1ra genes (Cominelli F, Bortolami M, Pizarro T, Monsacchi L, Ferretti M, Brewer M, Eisenberg S, and Ng R, Rabbit Interleukin-1 Receptor Antagonist. *J. of Biol. Chem.* 1994; 269: 6962–6971; Eisenberg S, Brewer M, Verderber E, Heimdal P, Brandhuber B, and Thompson R, Interleukin 1 receptor antagonist is a member of the interleukin 1 gene family: Evolution of a cytokine control mechanism, *Immunology* 1991; 88: 5232–5236) and described as a common organization to IL-1 family members (Zahedi K, Uhlar C, Rits M, Prada A, and Whitehead A, The mouse interleukin 1 receptor antagonist protein: Gene structure and regulation in vitro. *Cytokine* 1994; 6: 1–9). The coding region sequence has 84% identity with the human IL-1ra sequence of the same region. The short 5' untranslated region has 58% similarity and the 3' UTR has 62% of similarity as compared to the human homologous.

The predicted amino acid sequence encoded by the canine IL-1ra gene is very similar to the sequences of the species above mentioned having 80% identity to the human protein. Thus, the receptor antagonist family demonstrates a very high level of conservation between these sequences. The N-terminal 25 amino acids are tentatively identified as the signal peptide. The canine sequence is similar to the other species in that the sequence at the position of the purported mature protein start in the canine, beginning RPLGKR, parallels the other species having a mature protein sequence starts beginning RPSGKR (mouse and rabbit), RPSGRK (human) and HPAGKR (rat). A mature protein beginning at this position results in a molecule having 151 amino acid residues and a predicted molecular weight of 16,610 KD.

Expression of Canine IL-1ra Protein

Figure 5:
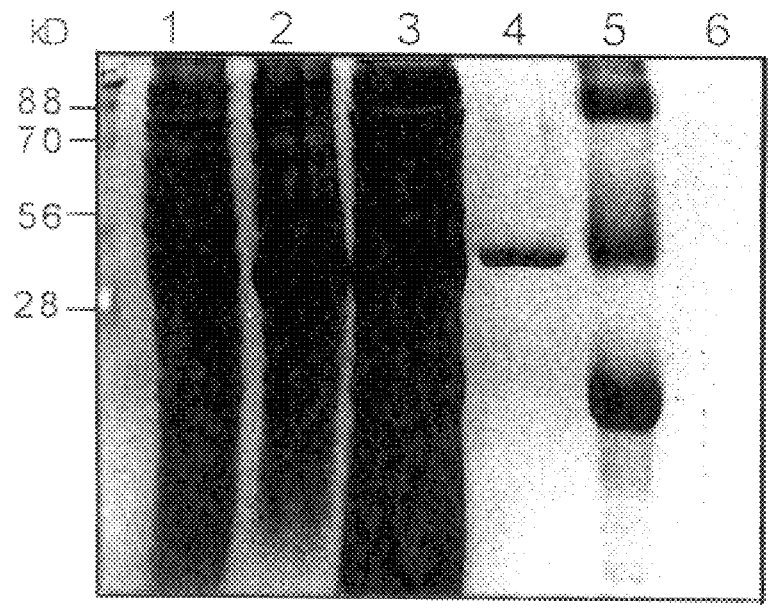
FIG. 5 is a PAGE gel showing expression of fusion peptide containing IL-1ra and the purified fusion protein expression product as well as the fusion product digested with thrombin.

The cDNA clone c IL-1ra was amplified by PCR using primers designated in SEQ ID Nos. 18 and 19. These primers were designed to generate a 5' Bgl II restriction site for use in cloning the gene into the Bam HI site of the GST fusion protein expression vector pGEX-2T (Phannacia), and a 3' EcoRI restriction site located downstream of the termination codon for cloning into the Eco RI site of the expression plasmid. The PCR product which was generated using these primers comprised a 495 base pair sequence of which (1) 456 base pairs encode the IL-1ra protein from the cystine at amino acid position 25 of the full length protein (nucleotide base 132), (2) the necessary amino acids glycine and serine 5' to the cystine for thrombin cleavage recognition, and (3) at the 3' end, natural sequence down stream of the termination codon into which an Eco RI restriction site had been engineered. The fusion protein construct was then expressed in *E. coli* strain DH5α- using IPTG induction methodology. FIG. 5 shows a 12% Coomassie brilliant blue stained SDS-PAGE of canine IL- 1ra fusion and cleaved protein product. The IL-1ra may be specifically cleaved from the fusion protein using thrombin according to standard techniques. Lane 1 shows cells sonicated before induction with IPTG. Lane 2 shows supernatant of cells sonicated after induction with IPTG and cell cultured for 5 hours in LB Broth (shaker culture). Lane 3 depicts a pellet of sonicated cells post IPTG induction. Lane 4 shows the fusion protein after elution from glutathione-sepharose column separation. As is clear, the protein may be isolated to substantially high purity as a fusion protein product. Lane 5 depicts flow through of glutathione-sepharose column loaded with supernatant of sonicated cells post IPTG induction. Lane 6 shows flow through of glutathione sepharose column loaded with fusion protein digested with thrombin. The free IL-1ra generates a band just under 19KD.

Purification of the IL-1ra Protein

Figure 6:
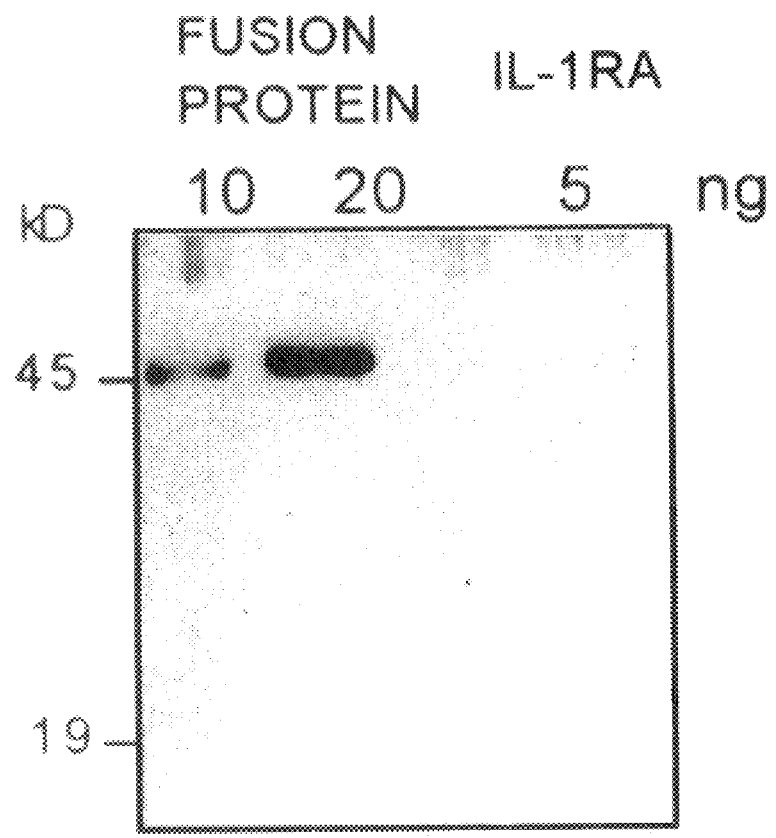
FIG. 6 is an western blot of both the purified IL-1ra fusion and cleaved proteins detected by an enhanced chemiluminescence (ECL) system.

The fusion protein was purified over a Glutathione-Sepharose column (1×10 cm). Following column separation, the IL-1ra portion was released by digestion of the fusion protein with human thrombin (1 mg/ml). As shown in FIG. 6 both the fusion protein and released IL-1ra were detected on SDS-PAGE western blot using chemiluminescence technique (Pierce Rockford, Ill.). The released protein may be obtained in highly pure form.

Antagonist Activity

The western blot methodology discussed above used goat anti-human IL-1ra antibody (R&D Systems Minneapolis, Minn.) and shows that canine IL-1ra amino acid sequence is very similar to the human protein having good immunological cross reactivity. Thus, one can expect likelihood that its metabolic activity in the dog may be similar to that of the human protein's activity in man.

In vitro test blocking of IL-1 by canine IL-1ra

Efficacy of the canine protein was tested indirectly by observation of its effect on the blocking of IL-6 mRNA induction in the THP-1 human monocyte cell line. It is well established that IL-1B induces the production of IL-6. Administration of IL-1B to these cells will induce IL-6 message. If IL-1B is blocked by administration of IL-1ra, then a drop in IL-6 message is observed as shown in table II (data in arbitrary units).

TABLE II

| Treatment of Cells | IL-6 message level |
| --- | --- |
| IL-1 | 12 |
| IL-1/IL-1ra | 4 |

Measurements of IL-6 mRNA were carried out by harvesting total RNA from treated cells followed by electrophoresis and Northern blot. The Northern blot was then exposed to a

BRIEF DESCRIPTION OF THE SEQUENCE LISTING

SEQ ID NO:1 is a nucleotide sequence showing the cDNA sequence obtained for canine IL-1ra. The open reading frame (ORF) of the IL-1ra protein is defined by nucleotide base number 60 to base number 587. The predicted signal peptide sequence is defined by amino acids −25 to −1. The mature peptide is defined by amino acids 1–151.

SEQ ID NO: 2 is an amino acid sequence of the signal peptide of IL-1ra protein.

SEQ ID NO: 3 is an amino acid sequence of the mature IL-1ra protein.

SEQ ID NO: 4 is an amino acid sequence of the full length IL-1ra protein.

SEQ ID NO: 5 is an amino acid sequence of the fusion protein after cleavage with thrombin.

SEQ ID NO: 6–SEQ ID NO 7 are oligonucleotides used as human primers to construct the probe use for screening the dog cDNA library.

SEQ ID NO: 8–SEQ ID NO:17 are oligonucleotides used to sequence the full length canine cDNA. Sequences 8, 9, and 15 anneal to m13 and read downstream for number 8 and upstream for numbers 9 and 15. The locations for internal primers are shown on FIG. 1.

SEQ ID NO: 18–SEQ ID NO: 19 are oligonucleotides used to construct a mature canine IL-1ra gene sequence by polymerase chain reaction (PCR).

SEQ ID NO: 20–SEQ ID NO: 23 are three letter code amino acid sequences for human, mouse, rabbit, and rat IL-1ra.

SEQ ID NO: 24–SEQ ID NO: 27 are nucleotide sequences for human, mouse, rabbit and rat IL-1ra.

SEQUENCE LISTING

```
(1) GENERAL INFORMATION:

(iii) NUMBER OF SEQUENCES: 27

(2) INFORMATION FOR SEQ ID NO:1:

(i) SEQUENCE CHARACTERISTICS:
         (A) LENGTH: 1710 base pairs
         (B) TYPE: nucleic acid
         (C) STRANDEDNESS: double
         (D) TOPOLOGY: linear (ii) MOLECULE TYPE: cDNA to mRNA (iii) HYPOTHETICAL: N (iv) ANTI-SENSE: N (vi) ORIGINAL SOURCE:
         (A) ORGANISM: Canis familiaris
         (B) CELL TYPE: canine peripheral blood macrophage
         (C) CELL LINE: primary monocytes (vii) IMMEDIATE SOURCE:
         (A) LIBRARY: lambda gt11 cDNA
         (B) CLONE: Canine IL-1ra (ix) FEATURE:
         (A) NAME/KEY: CDS
         (B) LOCATION: 1 to 1710
         (C) OTHER INFORMATION:

(ix) FEATURE:
         (A) NAME/KEY: open reading frame
         (B) LOCATION: 60 to 587
         (C) OTHER INFORMATION:

(xi) SEQUENCE DESCRIPTION: SEQ ID NO:1:

ACGGCTGCGA GAAGACGACA GAAGGGGCA GTGTCCCGTT GCCTCGCTGT                      50

GGCCACCGA  ATG GAA ACC TGC AGG TGT CCT CTC AGC TAC CTA                    92
           Met Glu Thr Cys Arg Cys Pro Leu Ser Tyr Leu
           -25              -20                 -15

ATC TCT TTC CTC CTT TTC CTG CCC CAT TCA GAG ACA GCC TGC                  134
Ile Ser Phe Leu Leu Phe Leu Pro His Ser Glu Thr Ala Cys
             -10              -5                -1

CGT CCC TTG GGG AAG AGA CCT TGC AGG ATG CAA GCC TTC AGA                  176
Arg Pro Leu Gly Lys Arg Pro Cys Arg Met Gln Ala Phe Arg
```

-continued

```
1               5                    10
ATC TGG GAT GTT AAC CAG AAG ACC TTC TAC CTG AGG AAT AAC        218
Ile Trp Asp Val Asn Gln Lys Thr Phe Tyr Leu Arg Asn Asn
15                  20                  25

CAA CTA GTC GCT GGA TAC TTG CAA GGA TCA AAT ACT AAA TTA        260
Gln Leu Val Ala Gly Tyr Leu Gln Gly Ser Asn Thr Lys Leu
        30                  35                  40

GAA GAG AAG TTA GAT GTG GTG CCC GTC GAG CCT CAT GCC GTG        302
Glu Glu Lys Leu Asp Val Val Pro Val Glu Pro His Ala Val
            45                  50                  55

TTC TTG GGG ATC CAT GGG GGG AAG CTG TGC CTG GCC TGT GTC        344
Phe Leu Gly Ile His Gly Gly Lys Leu Cys Leu Ala Cys Val
                60                  65                  70

AAG TCT GGA GAT GAG ACC AGG CTC CAG CTG GAG GCC GTT AAC        386
Lys Ser Gly Asp Glu Thr Arg Leu Gln Leu Glu Ala Val Asn
                    75                  80

ATC ACT GAC CTG AGT AAG AAC AAG GAT CAA GAC AAG CGC TTT        428
Ile Thr Asp Leu Ser Lys Asn Lys Asp Gln Asp Lys Arg Phe
85                  90                  95

ACC TTC ATC CTC TCA GAC AGT GGC CCC ACC ACC AGC TTT GAG        470
Thr Phe Ile Leu Ser Asp Ser Gly Pro Thr Thr Ser Phe Glu
        100                 105                 110

TCT GCT GCC TGC CCT GGC TGG TTC CTC TGC ACA GCA CTG GAG        512
Ser Ala Ala Cys Pro Gly Trp Phe Leu Cys Thr Ala Leu Glu
            115                 120                 125

GCC GAC CGG CCT GTC AGC CTC ACC AAC AGA CCA GAA GAG GCC        554
Ala Asp Arg Pro Val Ser Leu Thr Asn Arg Pro Glu Glu Ala
                130                 135                 140

ATG ATG GTC ACT AAG TTC TAC TTC CAG AAG GAA TAA                590
Met Met Val Thr Lys Phe Tyr Phe Gln Lys Glu
                    145                 150 151

TAGTGTGTCC ATTCCGTGCT TCCCCCCCAC TCCCAACACA TCAATGACTC          640

CAGAGATGCC TCTCCATTCT GCCTGGGGTC TCCTGGCTGT GGTGGAGGCT          690

CTGAGGAGCA GCCTCGGTGG GGTGGACCCT CAGAAGGATG TATGAGAGCC          740

CTGGTAACGG GACCCTGCCT CCAGCCTCCT CAGCTAGCCA ACCTCAATGC          790

TGCCACCACA GTGGTCTTTC TAAAGTGCAC CTCTAGCTGC AGCACTGCTC          840

CAGGCCTTTC AGGGCTGCCT CTGCCTTCTG GATTAAAGCC AGGCTGCTTG          890

GCCAGCCTGG CCCCCTGCTC TCCTCTCCGT AACTCCTTGC TCTCCTCCCT          940

TGCCCCATGT CCATGTCCTG GATCCCTCCT GCCCCTTTGC TGGCCTCCCA          990

AACCTTGTGT TTTGCAAACC GATGCTGTTC TGTGGGAAA CCTTAGAGTC          1040

TGTGCCAAGA TGGCCGCTAA GGATTTCAAC TTGGCTTTCC TTTGAAGCCA         1090

ATTTCATCCA GTTTCAAGGG AGAGTCCTTT ATTTAGACAC TATGTCCATT         1140

CTGGAAAAGT GTGGGCAAGG ATGAAAAGTA GCTCTCCCTT TTGATTTCTC         1190

TTATTTTTGA ACGTCCTGAC CTGCAAAAAT GACAAGTTAG TGTGTTATGT         1240

TGGTCTCTAC TTTTTTTCTT TCTGTGATGT TCCTAAAGCC TGGCCCCACT         1290

GCTCCAGCGA GGTACCATTT CCACTCCAGG CCTTTGACAG CCACCTGCAG         1340

TGCTTGTCCT CCCCATCTCT CCCATCAAAA CTCCCAGCTG CAGGCCAGGG         1390

CATCAATGTG GCTCCACTGT TCCTGGGAGG GAGGAATTAC TCTCGGACCA         1440

TTTTACACTT CTGACACTCT GAGACTTGTT TGAAAGGTTG TGTCTCTGTC         1490

TGTCTCCCAC ACCAGACTGT GAGTTCCCAA GAGAAGGGAG CATGACCTCT         1540
```

```
GTGTTTTGGG GCTCCCGCAG GGCTGAGCAC ACAGCTCCGG CCCTTAGCAC         1590

GTGCTCACTG AATGTGTGTT GTATGTGTTG AGTAGAAAGG TTTTTACTTT         1640

TTGTGAATTA AGGTTTGTTT TACAATAAAA TTTTAAAAAT TCAAAAAAAA         1690

AAAAAAAAAA AAAAAAAAA                                          1710

(2) INFORMATION FOR SEQ ID NO:2:

(i) SEQUENCE CHARACTERISTICS:
        (A) LENGTH: 25 amino acids
        (B) TYPE: amino acid
        (D) TOPOLOGY: linear (ii) MOLECULE TYPE: signal peptide (xi) SEQUENCE DESCRIPTION: SEQ ID NO:2:

Met Glu Thr Cys Arg Cys Pro Leu Ser Tyr Leu
-25              -20              -15

Ile Ser Phe Leu Leu Phe Leu Pro His Ser Glu Thr Ala Cys
            -10              -5              -1

(2) INFORMATION FOR SEQ ID NO:3:

(i) SEQUENCE CHARACTERISTICS:
        (A) LENGTH: 151 amino acids
        (B) TYPE: amino acid
        (D) TOPOLOGY: linear (ii) MOLECULE TYPE: mature peptide (xi) SEQUENCE DESCRIPTION: SEQ ID NO:3:

Arg Pro Leu Gly Lys Arg Pro Cys Arg Met Gln Ala Phe Arg
1             5                 10

Ile Trp Asp Val Asn Gln Lys Thr Phe Tyr Leu Arg Asn Asn
15              20              25

Gln Leu Val Ala Gly Tyr Leu Gln Gly Ser Asn Thr Lys Leu
        30              35              40

Glu Glu Lys Leu Asp Val Val Pro Val Glu Pro His Ala Val
        45              50              55

Phe Leu Gly Ile His Gly Gly Lys Leu Cys Leu Ala Cys Val
            60              65              70

Lys Ser Gly Asp Glu Thr Arg Leu Gln Leu Glu Ala Val Asn
            75              80

Ile Thr Asp Leu Ser Lys Asn Lys Asp Gln Asp Lys Arg Phe
85              90              95

Thr Phe Ile Leu Ser Asp Ser Gly Pro Thr Thr Ser Phe Glu
    100             105             110

Ser Ala Ala Cys Pro Gly Trp Phe Leu Cys Thr Ala Leu Glu
        115             120             125

Ala Asp Arg Pro Val Ser Leu Thr Asn Arg Pro Glu Glu Ala
            130             135             140

Met Met Val Thr Lys Phe Tyr Phe Gln Lys Glu
            145             150 151

(2) INFORMATION FOR SEQ ID NO:4:

(i) SEQUENCE CHARACTERISTICS:
        (A) LENGTH: 176 amino acids
        (B) TYPE: amino acid
        (D) TOPOLOGY: linear
```

(ii) MOLECULE TYPE: IL-1ra full length peptide (xi) SEQUENCE DESCRIPTION: SEQ ID NO:4:

```
    Met Glu Thr Cys Arg Cys Pro Leu Ser Tyr Leu
    -25             -20             -15

Ile Ser Phe Leu Leu Phe Leu Pro His Ser Glu Thr Ala Cys
            -10             -5                      -1

Arg Pro Leu Gly Lys Arg Pro Cys Arg Met Gln Ala Phe Arg
1               5               10

Ile Trp Asp Val Asn Gln Lys Thr Phe Tyr Leu Arg Asn Asn
15              20              25

Gln Leu Val Ala Gly Tyr Leu Gln Gly Ser Asn Thr Lys Leu
            30              35              40

Glu Glu Lys Leu Asp Val Val Pro Val Glu Pro His Ala Val
            45              50              55

Phe Leu Gly Ile His Gly Gly Lys Leu Cys Leu Ala Cys Val
            60              65              70

Lys Ser Gly Asp Glu Thr Arg Leu Gln Leu Glu Ala Val Asn
            75              80

Ile Thr Asp Leu Ser Lys Asn Lys Asp Gln Asp Lys Arg Phe
85              90              95

Thr Phe Ile Leu Ser Asp Ser Gly Pro Thr Thr Ser Phe Glu
    100             105             110

Ser Ala Ala Cys Pro Gly Trp Phe Leu Cys Thr Ala Leu Glu
            115             120             125

Ala Asp Arg Pro Val Ser Leu Thr Asn Arg Pro Glu Glu Ala
            130             135             140

Met Met Val Thr Lys Phe Tyr Phe Gln Lys Glu
            145             150 151
```

(2) INFORMATION FOR SEQ ID NO:5:

(i) SEQUENCE CHARACTERISTICS:
       (A) LENGTH: 154 amino acids
       (B) TYPE: amino acid
       (D) TOPOLOGY: linear (ii) MOLECULE TYPE: cleaved IL-1ra peptide from fusion construct (xi) SEQUENCE DESCRIPTION: SEQ ID NO:5:

```
Gly Ser Cys Arg Pro Leu Gly Lys Arg Pro Cys Arg Met Gln Ala
1               5               10              15

Phe Arg Ile Trp Asp Val Asn Gln Lys Thr Phe Tyr Leu Arg Asn
            20              25              30

Asn Gln Leu Val Ala Gly Tyr Leu Gln Gly Ser Asn Thr Lys Leu
            35              40              45

Glu Glu Lys Leu Asp Val Val Pro Val Glu Pro His Ala Val Phe
            50              55              60

Leu Gly Ile His Gly Gly Lys Leu Cys Leu Ala Cys Val Lys Ser
            65              70              75

Gly Asp Glu Thr Arg Leu Gln Leu Glu Ala Val Asn Ile Thr Asp
            80              85              90

Leu Ser Lys Asn Lys Asp Gln Asp Lys Arg Phe Thr Phe Ile Leu
            95              100             105

Ser Asp Ser Gly Pro Thr Thr Ser Phe Glu Ser Ala Ala Cys Pro
            110             115             120
```

-continued

```
Gly Trp Phe Leu Cys Thr Ala Leu Glu Ala Asp Arg Pro Val Ser
            125                 130                 135

Leu Thr Asn Arg Pro Glu Glu Ala Met Met Val Thr Lys Phe Tyr
            140                 145                 150

Phe Gln Lys Glu
            154
```

(2) INFORMATION FOR SEQ ID NO:6:

(i) SEQUENCE CHARACTERISTICS:
        (A) LENGTH:33 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:6:

CCCTCTGGGA GAAAATCCAG CAAGATGCAA GCC         33

(2) INFORMATION FOR SEQ ID NO:7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:7:

CTACTCGTCC TCCTGGAAGT AGAA         24

(2) INFORMATION FOR SEQ ID NO:8:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:8:

GTAAAACGAC GGCCAGT         17

(2) INFORMATION FOR SEQ ID NO:9:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE:oligonucleotide (xi) SEQUENCE DESCRIPTION: SEQ ID NO:9:

AACAGCTATG ACCATG         16

(2) INFORMATION FOR SEQ ID NO:10:

(i) SEQUENCE CHARACTERISTICS:
        (A) LENGTH: 23 basepairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:10:

CAGCCTCGGT GGGGTGGACC CTC                                              23

(2) INFORMATION FOR SEQ ID NO:11:

(i) SEQUENCE CHARACTERISTICS:
            (A) LENGTH: 23 base pairs
            (B) TYPE: nucleic acid
            (B) STRANDEDNESS: single
            (D) TOPOLOGY: linear (ii) MOLECULE TYPE: oligonucleotide (xi) SEQUENCE DESCRIPTION: SEQ ID NO:11:

TTGATGGGAG AGTGGGGGGA GGA                                              23

(2) INFORMATION FOR SEQ ID NO:12:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: oligonucleotide (xi) SEQUENCE DESCRIPTION: SEQ ID NO:12:

TCTGGGATGT TAACCAGAAG ACCT                                             24

(2) INFORMATION FOR SEQ ID NO:13:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: oligonucleotide (xi) SEQUENCE DESCRIPTION: SEQ ID NO:13:

ACTCAACACA TACAACACAC ATTC                                             24

(2) INFORMATION FOR SEQ ID NO:14:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: oligonucleotide (xi) SEQUENCE DESCRIPTION: SEQ ID NO:14:

CTCAGACAGT GGCCCCACCA CCAG                                             24

(2) INFORMATION FOR SEQ ID NO:15:

(i) SEQUENCE CHARACTERISTICS:
            (A) LENGTH: 24 basepairs
            (B) TYPE: nucleic acid
            (C) STRANDEDNESS: single
            (D) TOPOLOGY: linear (ii) MOLECULE TYPE: oligonucleotide (xi) SEQUENCE DESCRIPTION: SEQ ID NO:15:

```
TTCATTCAGC TCCGGGGTAC CGAG                                                    24

(2) INFORMATION FOR SEQ ID NO:16:

(i) SEQUENCE CHARACTERISTICS:
         (A) LENGTH: 24 basepairs
         (B) TYPE: nucleic acid
         (C) STRANDEDNESS: single
         (D) TOPOLOGY: linear (ii) MOLECULE TYPE:oligonucleotide (xi) SEQUENCE DESCRIPTION: SEQ ID NO:16:

GAGATGAGAC CAGGCTCCAG CTGG                                                    24

(2) INFORMATION FOR SEQ ID NO:17:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: oligonucleotide (xi) SEQUENCE DESCRIPTION: SEQ ID NO:17:

GCCGACCGGC CTGTCAGCCT CACC                                                    24

(2) INFORMATION FOR SEQ ID NO:18:

(i) SEQUENCE CHARACTERISTICS:
         (A) LENGTH: 35 base pairs
         (B) TYPE: nucleic acid
         (C) STRANDEDNESS: single
         (D) TOPOLOGY: linear (ii) MOLECULE TYPE: oligonucleotide (xi) SEQUENCE DESCRIPTION: SEQ ID NO:18:

GAGAGATCTT GCCGTCCCTT GGGGAAGAGA CCTTG                                        35

(2) INFORMATION FOR SEQ ID NO:19:

(i) SEQUENCE CHARACTERISTICS:
         (A) LENGTH: 33 base pairs
         (B) TYPE: nucleic acid
         (C) STRANDEDNESS: single
         (D) TOPOLOGY: linear (ii) MOLECULE TYPE: oligonucleotide (xi) SEQUENCE DESCRIPTION: SEQ ID NO:19:

GGGGGGGAAT TCCGGAATGG ACACACTATT ATT                                          33

(2) INFORMATION FOR SEQ ID NO:20:

(i) SEQUENCE CHARACTERISTICS:
         (A) LENGTH: 177 amino acids
         (B) TYPE: amino acid
         (C) STRANDEDNESS: single
         (D) TOPOLOGY: linear (ii) MOLECULE TYPE: human IL-1ra sequence (xi) SEQUENCE DESCRIPTION: SEQ ID NO: 20:

Met Glu Ile Cys Arg Gly Leu Arg Ser His Leu Ile Thr Leu Leu
1               5                   10                  15

Leu Phe Leu Phe His Ser Glu Thr Ile Cys Arg Pro Ser Gly Arg
```

```
                        20                  25                  30
Lys Ser Ser Lys Met Gln Ala Phe Arg Ile Trp Asp Val Asn Gln
                35                  40                  45
Lys Thr Phe Tyr Leu Arg Asn Asn Gln Leu Val Ala Gly Tyr Leu
                50                  55                  60
Gln Gly Pro Asn Val Asn Leu Glu Glu Lys Ile Asp Val Val Pro
                65                  70                  75
Ile Glu Pro His Ala Leu Phe Leu Gly Ile His Gly Gly Lys Met
                80                  85                  90
Cys Leu Ser Cys Val Lys Ser Gly Asp Glu Thr Arg Leu Gln Leu
                95                 100                 105
Glu Ala Val Asn Ile Thr Asp Leu Ser Glu Asn Arg Lys Gln Asp
               110                 115                 120
Lys Arg Phe Ala Phe Ile Arg Ser Asp Ser Gly Pro Thr Thr Ser
               125                 130                 135
Phe Glu Ser Ala Ala Cys Pro Gly Trp Phe Leu Cys Thr Ala Met
               140                 145                 150
Glu Ala Asp Gln Pro Val Ser Leu Thr Asn Met Pro Asp Glu Gly
               155                 160                 165
Val Met Val Thr Lys Phe Tyr Phe Gln Glu Asp Glu
               170                 175     177

(2) INFORMATION FOR SEQ ID NO:21:

(i) SEQUENCE CHARACTERISTICS:
        (A) LENGTH: 178 amino acids
        (B) TYPE: amino acid
        (C) STRANDEDNESS: single
        (D) TOPOLOGY: linear (ii) MOLECULE TYPE: mouse IL-1ra sequence (xi) SEQUENCE DESCRIPTION: SEQ ID NO:21:

Met Glu Ile Cys Trp Gly Pro Tyr Ser His Leu Ile Ser Leu Leu
1               5                  10                  15
Leu Ile Leu Leu Phe His Ser Glu Ala Ala Cys Arg Pro Ser Gly
                20                  25                  30
Lys Arg Pro Cys Lys Met Gln Ala Phe Arg Ile Trp Asp Thr Asn
                35                  40                  45
Gln Lys Thr Phe Tyr Leu Arg Asn Asn Gln Leu Ile Ala Gly Tyr
                50                  55                  60
Leu Gln Gly Pro Asn Ile Lys Leu Glu Gly Lys Ile Asp Met Val
                65                  70                  75
Pro Ile Asp Leu His Ser Val Phe Leu Gly Ile His Gly Gly Lys
                80                  85                  90
Leu Cys Leu Ser Cys Ala Lys Ser Gly Asp Asp Ile Lys Leu Gln
                95                 100                 105
Leu Glu Glu Val Asn Ile Thr Asp Leu Ser Lys Asn Lys Glu Glu
               110                 115                 120
Asp Lys Arg Phe Thr Phe Ile Arg Ser Glu Lys Gly Pro Thr Thr
               125                 130                 135
Ser Phe Glu Ser Ala Ala Cys Pro Gly Trp Phe Leu Cys Thr Thr
               140                 145                 150
Leu Glu Ala Asp Arg Pro Val Ser Leu Thr Asn Thr Pro Glu Glu
               155                 160                 165
Pro Leu Ile Val Thr Lys Phe Tyr Phe Gln Glu Asp Gln
```

```
            170             175         178

(2) INFORMATION FOR SEQ ID NO:22:

(i) SEQUENCE CHARACTERISTICS:
        (A) LENGTH: 177 amino acids
        (B) TYPE: amino acid
        (C) STRANDEDNESS: single
        (D) TOPOLOGY: linear (ii) MOLECULE TYPE: rabbit IL-1ra sequence (xi) SEQUENCE DESCRIPTION: SEQ ID NO:22:

Met Arg Pro Ser Arg Ser Thr Arg Arg His Leu Ile Ser Leu Leu
1               5                   10                  15

Leu Phe Leu Phe His Ser Glu Thr Ala Cys Arg Pro Ser Gly Lys
                20                  25                  30

Arg Pro Cys Arg Met Gln Ala Phe Arg Ile Trp Asp Val Asn Gln
                35                  40                  45

Lys Thr Phe Tyr Leu Arg Asn Asn Gln Leu Val Ala Gly Tyr Leu
                50                  55                  60

Gln Gly Pro Asn Ala Lys Leu Glu Glu Arg Ile Asp Val Val Pro
                65                  70                  75

Leu Glu Pro Gln Leu Leu Phe Leu Gly Ile Gln Arg Gly Lys Leu
                80                  85                  90

Cys Leu Ser Cys Val Lys Ser Gly Asp Lys Met Lys Leu His Leu
                95                  100                 105

Glu Ala Val Asn Ile Thr Asp Leu Gly Lys Asn Lys Glu Gln Asp
                110                 115                 120

Lys Arg Phe Thr Phe Ile Arg Ser Asn Ser Gly Pro Thr Thr Thr
                125                 130                 135

Phe Glu Ser Ala Ser Cys Pro Gly Trp Phe Leu Cys Thr Ala Leu
                140                 145                 150

Glu Ala Asp Gln Pro Val Ser Leu Thr Asn Thr Pro Asp Asp Ser
                155                 160                 165

Ile Val Val Thr Lys Phe Tyr Phe Gln Glu Asp Gln
                170                 175     177

(2) INFORMATION FOR SEQ ID NO:23:

(i) SEQUENCE CHARACTERISTICS:
        (A) LENGTH: 178 amino acids
        (B) TYPE: amino acid
        (C) STRANDEDNESS: single
        (D) TOPOLOGY: linear (ii) MOLECULE TYPE: rat IL-1ra sequence (xi) SEQUENCE DESCRIPTION: SEQ ID NO:23:

Met Glu Ile Cys Arg Gly Pro Tyr Ser His Leu Ile Ser Leu Leu
1               5                   10                  15

Leu Ile Leu Leu Phe Arg Ser Glu Ser Ala Gly His Pro Ala Gly
                20                  25                  30

Lys Arg Pro Cys Lys Met Gln Ala Phe Arg Ile Trp Asp Thr Asn
                35                  40                  45

Gln Lys Thr Phe Tyr Leu Arg Asn Asn Gln Leu Ile Ala Gly Tyr
                50                  55                  60

Leu Gln Gly Pro Asn Thr Lys Leu Glu Glu Lys Ile Asp Met Val
                65                  70                  75
```

```
Pro Ile Asp Phe Arg Asn Val Phe Leu Gly Ile His Gly Gly Lys
            80                  85                  90

Leu Cys Leu Ser Cys Val Lys Ser Gly Asp Asp Thr Lys Leu Gln
            95                 100                 105

Leu Glu Glu Val Asn Ile Thr Asp Leu Asn Lys Asn Lys Glu Glu
           110                 115                 120

Asp Lys Arg Phe Thr Phe Ile Arg Ser Glu Thr Gly Pro Thr Thr
           125                 130                 135

Ser Phe Glu Ser Leu Ala Cys Pro Gly Trp Phe Leu Cys Thr Thr
           140                 145                 150

Leu Glu Ala Asp His Pro Val Ser Leu Thr Asn Thr Pro Lys Glu
           155                 160                 165

Pro Cys Thr Val Thr Lys Phe Tyr Phe Gln Glu Asp Gln
           170                 175         178

(2) INFORMATION FOR SEQ ID NO:24:

(i) SEQUENCE CHARACTERISTICS:
        (A) LENGTH: 534 base pairs
        (B) TYPE: nucleic acid
        (C) STRANDEDNESS: single
        (D) TOPOLOGY: linear (ii) MOLECULE TYPE: human IL-1ra DNA sequence (xi) SEQUENCE DESCRIPTION: SEQ ID NO:24:

ATGGAAATCT   GCAGAGGCCT   CCGCAGTCAC   CTAATCACTC                40

TCCTCCTCTT   CCTGTTCCAT   TCAGAGACGA   TCTGCCGACC                80

CTCTGGGAGA   AAATCCAGCA   AGATGCAAGC   CTTCAGAATC               120

TGGGATGTTA   ACCAGAAGAC   CTTCTATCTG   AGGAACAACC               160

AACTAGTTGC   TGGATACTTG   CAAGGACCAA   ATGTCAATTT               200

AGAAGAAAAG   ATAGATGTGG   TACCCATTGA   GCCTCATGCT               240

CTGTTCTTGG   GAATCCATGG   AGGGAAGATG   TGCCTGTCCT               280

GTGTCAAGTC   TGGTGATGAG   ACCAGACTCC   AGCTGGAGGC               320

AGTTAACATC   ACTGACCTGA   GCGAGAACAG   AAAGCAGGAC               360

AAGCGCTTCG   CCTTCATCCG   CTCAGACAGT   GGCCCCACCA               400

CCAGTTTTGA   GTCTGCCGCC   TGCCCCGGTT   GGTTCCTCTG               440

CACAGCGATG   GAAGCTGACC   AGCCCGTCAG   CCTCACCAAT               480

ATGCCTGACG   AAGGCGTCAT   GGTCACCAAA   TTCTACTTCC               520

AGGAGGACGA   GTAG                                               534

(2) INFORMATION FOR SEQ ID NO:25:

(i) SEQUENCE CHARACTERISTICS:
        (A) LENGTH: 537 base pairs
        (B) TYPE: nucleic acid
        (C) STRANDEDNESS: single
        (D) TOPOLOGY: linear (ii) MOLECULE TYPE: mouse IL-1ra DNA sequence (xi) SEQUENCE DESCRIPTION: SEQ ID NO:25:

ATGGAAATCT   GCTGGGACC    CTACAGTCAC   CTAATCTCTC                40

TCCTTCTCAT   CCTTCTGTTT   CATTCAGAGG   CAGCCTGCCG                80
```

| | | | | |
|---|---|---|---|---|
| CCCTTCTGGG | AAAAGACCCT | GCAAGATGCA | AGCCTTCAGA | 120 |
| ATCTGGGATA | CTAACCAGAA | GACCTTTTAC | CTGAGAAACA | 160 |
| ACCAGCTCAT | TGCTGGGTAC | TTACAAGGAC | CAAATATCAA | 200 |
| ACTAGAAGAA | AAGATAGACA | TGGTGCCTAT | TGACCTTCAT | 240 |
| AGTGTGTTCT | TGGGCATCCA | CGGGGGCAAG | CTGTGCCTGT | 280 |
| CTTGTGCCAA | GTCTGGAGAT | GATATCAAGC | TCCAGCTGGA | 320 |
| GGAAGTTAAC | ATCACTGATC | TGAGCAAGAA | CAAAGAAGAA | 360 |
| GACAAGCGCT | TTACCTTCAT | CCGCTCTGAG | AAAGGCCCCA | 400 |
| CCACCAGCTT | TGAGTCAGCT | GCCTGTCCAG | GATGGTTCCT | 440 |
| CTGCACAACA | CTAGAGGCTG | ACCGTCCTGT | GAGCCTCACC | 480 |
| AACACACCGG | AAGAGCCCCT | TATAGTCACG | AAGTTCTACT | 520 |
| TCCAGGAAGA | CCAATAG | | | 537 |

(2) INFORMATION FOR SEQ ID NO:26:

(i) SEQUENCE CHARACTERISTICS:
        (A) LENGTH: 534 base pairs
        (B) TYPE: nucleic acid
        (C) STRANDEDNESS: single
        (D) TOPOLOGY: linear (ii) MOLECULE TYPE: rabbit IL-1ra DNA sequence (xi) SEQUENCE DESCRIPTION: SEQ ID NO:26:

| | | | | |
|---|---|---|---|---|
| ATGAGACCCT | CCAGGAGCAC | CCGCAGGCAC | CTAATCTCCC | 40 |
| TCCTCCTCTT | CCTGTTCCAT | TCAGAGACAG | CCTGCCGCCC | 80 |
| TTCTGGGAAA | AGACCTTGCA | GGATGCAGGC | CTTCAGAATC | 120 |
| TGGGATGTTA | ACCAGAAGAC | CTTCTACTTG | AGAAACAACC | 160 |
| AACTAGTCGC | TGGTTACTTG | CAAGGCCCAA | ATGCCAAATT | 200 |
| AGAAGAAAGG | ATAGATGTGG | TGCCCCTTGA | GCCTCAGCTC | 240 |
| CTGTTCCTGG | GCATCCAGAG | GGGGAAGTTG | TGCCTGTCTT | 280 |
| GTGTGAAGTC | TGGGGATAAG | ATGAAGCTCC | ATTTGGAGGC | 320 |
| CGTTAACATC | ACTGACCTGG | GCAAGAACAA | GGAGCAGGAC | 360 |
| AAGCGCTTCA | CCTTCATCCG | CTCCAATAGT | GGCCCTACCA | 400 |
| CCACCTTCGA | GTCTGCCTCC | TGCCCGGGCT | GGTTTCTCTG | 440 |
| CACGGCCCTG | GAGGCTGACC | AGCCGGTCAG | CCTCACCAAC | 480 |
| ACCCCGGACG | ACTCCATCGT | GGTCACCAAG | TTCTACTTCC | 520 |
| AGGAGGACCA | GTAG | | | 534 |

(2) INFORMATION FOR SEQ ID NO:27:

(i) SEQUENCE CHARACTERISTICS:
        (A) LENGTH: 537 base pairs
        (B) TYPE: nucleic acid
        (C) STRANDEDNESS: single
        (D) TOPOLOGY: linear (ii) MOLECULE TYPE: rat IL-1ra DNA sequence (xi) SEQUENCE DESCRIPTION: SEQ ID NO:27:

| | | | | |
|---|---|---|---|---|
| ATGGAAATCT | GCAGGGGACC | TTACAGTCAC | CTAATCTCTC | 40 |

-continued

```
TCCTTCTCAT  CCTTCTGTTT  CGTTCAGAGT  CAGCTGGCCA              80

CCCTGCTGGG  AAAAGACCCT  GCAAGATGCA  AGCCTTCAGA             120

ATCTGGGATA  CTAACCAGAA  GACCTTCTAC  CTGAGGAACA             160

ACCAGCTCAT  TGCTGGGTAC  TTACAAGGAC  CAAATACCAA             200

ACTAGAAGAA  AAGATAGACA  TGGTGCCTAT  TGACTTTCGG             240

AATGTGTTCT  TGGGCATCCA  CGGGGGCAAG  CTGTGCCTGT             280

CTTGTGTCAA  GTCTGGAGAT  GACACCAAGC  TCCAGCTGGA             320

GGAGGTTAAC  ATCACTGATC  TGAACAAGAA  CAAAGAAGAA             360

GACAAGCGCT  TTACCTTCAT  CCGCTCCGAG  ACAGGCCCTA             400

CCACCAGCTT   CGAATCACTT GCCTGTCCAG  GATGGTTCCT             440

CTGCACAACA   CTAGAGGCTG ATCATCCCGT  GAGCCTCACC             480

AACACACCAA  AAGAGCCCTG  TACAGTCACA  AAGTTCTACT             520

TCCAGGAAGA   CCAATAG                                       537
```

All prior art papers disclosed herein are hereby incorporated by reference. Modifications and other embodiments of the invention will be apparent to those skilled in the art to which this invention relates having the benefit of the foregoing teachings, descriptions, and associated drawings. The present invention is therefore not to be limited to the specific embodiments disclosed but is to include modifications and other embodiments which are within the scope of the appended claims.

What is claimed is:

1. An isolated DNA comprising a cDNA clone having a nucleotide sequence encoding an amino acid sequence selected from the group consisting of SEQ ID NO.: 3, SEQ ID NO.: 4, and SEQ ID. NO.: 5.

2. The isolated DNA of claim 1 wherein the amino acid is SEQ ID No.: 3.

3. The isolated DNA of claim 1 wherein the amino acid is SEQ ID No.: 4.

4. The isolated DNA of claim 1 wherein the amino acid is SEQ ID No.: 5.

5. An isolated DNA comprising a DNA having a sequence which is degenerate as a result of genetic code to a DNA as defined in claim 1 and which encodes a biologically active canine Il-1ra molecule.

6. An isolated DNA according to claim 1 which encodes a soluble canine Il-1ra molecule.

7. An isolated DNA according to claim 5 which encodes a soluble canine Il-1ra molecule.

8. The isolated DNA according to claim 1 wherein said DNA is expressed by a recombinant expression vector.

9. The isolated DNA according to claim 5 wherein said DNA is expressed by a recombinant expression vector.

10. The isolated DNA according to claim 6 wherein said DNA is expressed by a recombinant expression vector.

11. The isolated DNA according to claim 7 wherein said DNA is expressed by a recombinant expression vector.

12. The isolated DNA according to claim 8, wherein the expression vector is pGEX-2T.

13. The isolated DNA according to claim 9, wherein the expression vector is pGEX-2T.

14. The isolated DNA according to claim 10, wherein the expression vector is pGEX-2T.

15. The isolated DNA according to claim 11, wherein the expression vector is pGEX-2T.

16. An isolated DNA comprising a cDNA having a nucleotide sequence encoding an amino acid sequence selected from the group consisting of SEQ ID NO.: 3, SEQ ID NO.: 4, and SEQ ID NO.: 5.

17. The isolated DNA of claim 16 wherein the amino acid sequence is SEQ ID NO.: 3.

18. The isolated DNA of claim 16 wherein the amino acid sequence is SEQ ID NO.: 4.

19. The isolated DNA of claim 16 wherein the amino acid sequence is SEQ ID NO.: 5.

20. An isolated DNA comprising a DNA having a sequence which is degenerate as a result of genetic code to a DNA as defined in claim 16 and which encodes a biologically active canine Il-1ra molecule.

21. The isolated DNA according to claim 16 which encodes a soluble canine Il-1ra molecule.

22. The isolated DNA according to claim 20 which encodes a soluble canine Il-1ra molecule.

23. The isolated DNA according to claim 16 wherein said DNA is expressed by a prokaryotic expression vector.

24. The isolated DNA according to claim 20 wherein said DNA is expressed by a prokaryotic expression vector.

25. The isolated DNA according to claim 21 wherein said DNA is expressed by a prokaryotic expression vector.

26. The isolated DNA according to claim 22 wherein said DNA is expressed by a prokaryotic expression vector.

27. The isolated DNA according to claim 23 wherein said vector is pGEX-2T.

28. The isolated DNA according to claim 24 wherein said vector is pGEX-2T.

29. The isolated DNA according to claim 25 wherein said vector is pGEX-2T.

30. The isolated DNA according to claim 26 wherein said vector is pGEX-2T.

* * * * *